United States Patent
Piot-Grosjean et al.

(10) Patent No.: US 7,037,944 B2
(45) Date of Patent: *May 2, 2006

(54) COMBINATION OF A CB1 RECEPTOR ANTAGONIST AND OF SIBUTRAMINE, THE PHARMACEUTICAL COMPOSITIONS COMPRISING THEM AND THEIR USE IN THE TREATMENT OF OBESITY

(75) Inventors: Odile Piot-Grosjean, Choisy le Roi (FR); Philippe Picaut, Fontenay aux Roses (FR); François Petitet, Creteil (FR)

(73) Assignee: Aventis Pharma S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/941,190

(22) Filed: Sep. 15, 2004

(65) Prior Publication Data

US 2005/0032773 A1    Feb. 10, 2005

Related U.S. Application Data

(62) Division of application No. 09/968,903, filed on Oct. 3, 2001, now abandoned.

(60) Provisional application No. 60/244,187, filed on Oct. 31, 2000.

(30) Foreign Application Priority Data

Oct. 4, 2000    (FR)    .................... 00 12646

(51) Int. Cl.
    *A61K 31/135*    (2006.01)
    *A61K 31/397*    (2006.01)

(52) U.S. Cl. .................. 514/646; 514/210.01

(58) Field of Classification Search ............... 514/646, 514/210.01, 210.19, 210.2, 210.21
    See application file for complete search history.

(56) References Cited

U.S. PATENT DOCUMENTS

| | | |
|---|---|---|
| 6,355,631 B1 | 3/2002 | Achard et al. |
| 6,479,479 B1 | 11/2002 | Achard et al. |
| 6,518,264 B1 | 2/2003 | Achard et al. |

FOREIGN PATENT DOCUMENTS

| | | |
|---|---|---|
| EP | 0576357 | 12/1993 |
| EP | 0656354 | 6/1995 |
| EP | 0658548 | 6/1995 |
| WO | WO 90/08110 | 6/1990 |
| WO | WO 96/02248 | 2/1996 |
| WO | WO 97/19063 | 5/1997 |
| WO | WO 98/18481 | 5/1998 |
| WO | WO 98/32441 | 7/1998 |
| WO | WO 98/37061 | 8/1998 |
| WO | WO 01/15609 | 3/2000 |
| WO | WO 00/46209 | 8/2000 |
| WO | WO 01/64634 | 9/2001 |

OTHER PUBLICATIONS

D. H. Ryan, et al, Sibutramine: A Novel New Agent for Obesity Treatment, Obesity Research (1995, pp. 559S-559S, vol. 3).
Fanghanel G., et al, A Clinical Trial of the Use of Sibutramine for the Treatment of Patients Suffering Essential Obesity, International Journal Of Obesity (2000, pp. 144-150, vol. 24).
G. A. Bray, et al, Sibutramine Produces Dose-Related Weight Loss, Obesity Research (1999, pp. 189-198, vol. 7).
G. Colombo, et al, Appetite Suppression and Weight Loss After the Cannabinoid Antagonist SR, 141716 Life Sciences (1998, pp. 113-117, vol. 63).
H. C. Jackson, et al, Comparison of the Effects of Sibutramine and Other Monoamine Reuptake Inhibitors on Food intake in the Rat, British Journal of Pharmacology (1997, pp. 1758-1762, vol. 121).
J. Simiand, et al, SR 141716, a CB1 Cannabinoid Receptor Antagonist, Selectively Reduces Sweet Food Intake in Marmoeet Behavioral Pharmacology (1998, pp. 179-181, vol. 9).
Jules Hirsch, Magic Bullet For Obesity, BMJ (1998, pp. 1136-1138, vol. 317).
M. Nakazi et al., Inhibition of Serotonin Release in the Mouse Brain Via Presynaptic Cannabinoid CB1 Receptors, Naunyn-Schmiedeberg's Arch Pharmacol (2000, pp. 19-24, vol. 361).

*Primary Examiner*—Phyllis G. Spivack
(74) *Attorney, Agent, or Firm*—Joseph Strupczewski

(57) ABSTRACT

The present invention relates to the combination of a CB1 receptor antagonist and of sibutramine, to the pharmaceutical compositions comprising them and to their use in the treatment of obesity.

11 Claims, No Drawings

COMBINATION OF A CB1 RECEPTOR ANTAGONIST AND OF SIBUTRAMINE, THE PHARMACEUTICAL COMPOSITIONS COMPRISING THEM AND THEIR USE IN THE TREATMENT OF OBESITY

The present invention relates to the combination of a CB1 receptor antagonist and of sibutramine, to the pharmaceutical compositions comprising them and to their use in the treatment of obesity.

CB1 receptor antagonists are known for their effect on food intake and their use as anorexigenic (G. Colombo et al., Life Sciences, 63 (8), 113–117 (1998); J. Siamand et al., Behavioural Pharmacol., 9, 179–181 (1998)).

Sibutramine (BTS 54524; N-{1-[1-(4-chlorophenyl)cyclobutyl]-3-methylbutyl}-N,N-dimethylamine; Meridia®, Reductil®), its hydrate and its pharmaceutically acceptable salts and in particular its hydrochloride reduces food intake and is of use in the treatment of obesity (WO 90/061110; D. H. Ryan et al., Obesity Research, 3 (4), 553 (1995); H. C. Jackson et al., British Journal of Pharmacology, 121, 1758 (1997); G. Fanghanel et al., Inter. J. Obes., 24 (2), 144 (2000); G. A. Bray et al., Obes. Res., 7 (2), 189 (1999)).

It has now been found that the combination of sibutramine, its hydrate and its pharmaceutically acceptable salts and of a CB1 receptor antagonist exhibits a synergistic effect in reducing food consumption and is thus of use in the treatment of obesity.

The combination can also comprise several CB1 receptor antagonists.

Use may in particular be made, among CB1 receptor antagonists, of the azetidine derivatives disclosed in WO 00/15609, WO 01/64633 and WO 01/64634 of formula:

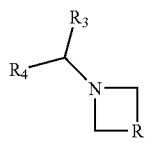

(I)

in which
either R represents a chain (A) or (B) and

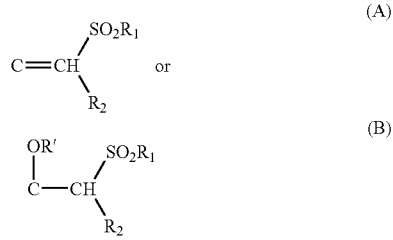

$R_1$ represents a methyl or ethyl radical, $R_2$ represents either an aromatic chosen from phenyl, naphthyl or indenyl, these aromatics being unsubstituted or substituted by one or more halogen, alkyl, alkoxy, —COalk, hydroxyl, —COOR$_5$, formyl, trifluoromethyl, trifluoromethylsulfanyl, trifluoromethoxy, nitro, —NR$_6$R$_7$, —CO—NH—NR$_6$R$_7$, —N(alk)COOR$_8$, cyano, —CONHR$_9$, —CO—NR$_{16}$R$_{17}$, alkylsulfanyl, hydroxyalkyl, —O-alk-NR$_{12}$R$_{13}$ or alkylthioalkyl, or a heteroaromatic chosen from the benzofuryl, benzothiazolyl, benzothienyl, benzoxazolyl, chromanyl, 2,3-dihydrobenzofuryl, 2,3-dihydrobenzothienyl, indolinyl, indolyl, isochromanyl, isoquinolyl, pyridyl, quinolyl, 1,2,3,4-tetrahydroisoquinolyl, 1,2,3,4-tetrahydroquinolyl, thiazolyl or thienyl rings, it being possible for these heteroaromatics to be unsubstituted or substituted by a halogen, alkyl, alkoxy, —COOR$_5$, trifluoromethyl, trifluoromethylsulfanyl, trifluoromethoxy, nitro, —NR$_6$R$_7$, —CO—NH—NR$_6$R$_7$, cyano, —CONHR$_9$, alkylsulfanyl, hydroxyalkyl or alkylthioalkyl, $R_3$ and $R_4$, which are identical or different, represent either an aromatic chosen from phenyl, naphthyl or indenyl, these aromatics being unsubstituted or substituted by one or more halogen, alkyl, alkoxy, formyl, hydroxyl, trifluoromethyl, trifluoromethoxy, —CO-alk, cyano, —COOR$_5$, —CONR$_{10}$R$_{11}$, —CO—NH—NR$_6$R$_7$, alkylsulfanyl, hydroxyalkyl, -alk-NR$_6$R$_7$ or alkylthioalkyl, or a heteroaromatic chosen from the benzofuryl, benzothiazolyl, benzothienyl, benzoxazolyl, chromanyl, 2,3-dihydrobenzofuryl, 2,3-dihydrobenzothienyl, furyl, isochromanyl, isoquinolyl, pyrrolyl, quinolyl, 1,2,3,4-tetrahydroisoquinolyl, thiazolyl or thienyl rings, it being possible for these heteroaromatics to be unsubstituted or substituted by a halogen, alkyl, alkoxy, hydroxyl, trifluoromethyl, trifluoromethoxy, cyano, —COOR$_5$, —CO—NH—NR$_6$R$_7$, —CONR$_{10}$R$_{11}$, -alk-NR$_6$R$_7$, alkylsulfanyl, hydroxyalkyl or alkylthioalkyl, $R_5$ is an alkyl radical or a phenyl radical optionally substituted by one or more halogen atoms, $R_6$ and $R_7$, which are identical or different, represent a hydrogen atom or an alkyl, —COOalk, cycloalkyl, alkylcycloalkyl, -alk-O-alk or hydroxyalkyl radical or else $R_6$ and $R_7$ form, together with the nitrogen atom to which they are attached, a saturated or unsaturated and mono- or bicyclic heterocycle having 3 to 10 ring members optionally comprising another heteroatom chosen from oxygen, sulfur and nitrogen and optionally being substituted by one or more alkyl, —COalk, —COOalk, —CO—NHalk, —CS—NHalk, —CO-alk-NR$_{14}$R$_{15}$, oxo, hydroxyalkyl, -alk-O-alk or —CO—NH$_2$ radicals, $R_8$ represents an alkyl radical, $R_9$ represents a hydrogen atom or a radical of the type alkyl or alkyl substituted by dialkylamino, phenyl, cycloalkyl (optionally substituted by —COOalk) or a saturated or unsaturated and mono- or bicyclic heterocycle having 3 to 10 ring members optionally comprising one or more heteroatoms chosen from oxygen, sulfur and nitrogen and optionally being substituted by one or more alkyl radicals, $R_{10}$ and $R_{11}$, which are identical or different, represent a hydrogen atom or an alkyl radical or else $R_{10}$ and $R_{11}$ form, together with the nitrogen atom to which they are attached, a saturated mono- or bicyclic heterocycle having 3 to 10 ring members optionally comprising another heteroatom chosen from oxygen, sulfur and nitrogen and optionally being substituted by an alkyl radical, $R_{12}$ and $R_{13}$, which are identical or different, represent a hydrogen atom or an alkyl or cycloalkyl radical or else $R_{12}$ and $R_{13}$ form, together with the nitrogen atom to which they are attached, a saturated mono- or bicyclic heterocycle having 3 to 10 ring members optionally comprising another heteroatom chosen from oxygen, sulfur and nitrogen and optionally being substituted by an alkyl, —COalk, —COOalk, —CO—NHalk, —CS—NHalk or —CO— alk-NR$_{14}$R$_{15}$ radical or a saturated mono- or bicyclic heterocycle having 3 to 10 ring members and comprising a heteroatom chosen from oxygen, sulfur and nitrogen, $R_{14}$ and $R_{15}$, which are identical or different, represent a hydrogen atom or an alkyl or —COOalk radical, $R_{16}$ and $R_{17}$ form, together with the nitrogen atom to which they are attached, a saturated mono- or bicyclic heterocycle having 3 to 10 ring members optionally comprising another heteroatom chosen from oxygen, sulfur and nitrogen, R' represents a hydrogen atom or a —CO-alk radical, or R represents a $CHR_{18}$ radical and $R_{18}$ represents an —$NHCOR_{19}$ or —$N(R_{20})$—Y—$R_{21}$ radical, Y is CO or $SO_2$, $R_4$ and $R_3$, which are identical or different, represent either an aromatic chosen from phenyl, naphthyl and indenyl, these aromatics being unsubstituted or substituted by one or more halogen, alkyl, alkoxy, formyl, hydroxyl, trifluoromethyl, trifluoromethoxy, —CO-alk, cyano, —COOH, —COOalk, —$CONR_{22}R_{23}$, —CO—NH—$NR_{24}R_{25}$, alkylsulfanyl, alkylsulfinyl, alkylsulfonyl, alkylsulfanylalkyl, alkylsulfinylalkyl, alkylsulfonylalkyl, hydroxyalkyl or -alk-$NH_{22}R_{23}$, or a heteroaromatic chosen from the benzofuryl, benzothiazolyl, benzothienyl, benzoxazolyl, chromanyl, 2,3-dihydrobenzofuryl, 2,3-dihydrobenzothienyl, pyrimidinyl, furyl, imidazolyl, isochromanyl, isoquinolyl, pyrrolyl, pyridyl, quinolyl, 1,2,3,4-tetrahydroisoquinolyl, thiazolyl and thienyl rings, it being possible for these heteroaromatics to be unsubstituted or substituted by a halogen, alkyl, alkoxy, hydroxyl, trifluoromethyl, trifluoromethoxy, cyano, —COOH, —COOalk, —CO—NH—$NR_{24}R_{25}$, —$CONR_{22}R_{23}$, -alk-$NR_{24}R_{25}$, alkylsulfanyl, alkylsulfinyl, alkylsulfonyl, alkylsulfanylalkyl, alkylsulfinylalkyl, alkylsulfonylalkyl or hydroxyalkyl, $R_{19}$ represents an -alk-$SO_2$—$R_{26}$ radical, an -alk-$SO_2$—CH=CH—$R_{26}$ radical, a $Het_1$ radical substituted by —$SO_2$—$R_{26}$ or a phenyl radical substituted by —$SO_2$—$R_{26}$ or -alk-$SO_2$—$R_{26}$, $R_{20}$ represents a hydrogen atom or an alkyl radical, $R_{21}$ represents a phenylalkyl, $Het_1$ or $Ar_1$ radical, $R_{22}$ and $R_{23}$, which are identical or different, represent a hydrogen atom or an alkyl radical or else $R_{22}$ and $R_{23}$ form, together with the nitrogen atom to which they are attached, a saturated mono- or bicyclic heterocycle having 3 to 10 ring members optionally comprising another heteroatom chosen from oxygen, sulfur and nitrogen and optionally being substituted by one or more alkyl, $R_{24}$ and $R_{25}$, which are identical or different, represent a hydrogen atom or an alkyl, —COOalk, cycloalkyl, alkylcycloalkyl, -alk-O-alk or hydroxyalkyl radical or else $R_{24}$ and $R_{25}$ form, together with the nitrogen atom to which they are attached, a saturated or unsaturated mono- or bicyclic heterocycle having 3 to 10 ring members optionally comprising another heteroatom chosen from oxygen, sulfur and nitrogen and optionally being substituted by one or more alkyl, —COalk, —COOalk, —CO—NHalk, —CS—NHalk, oxo, hydroxyalkyl, -alk-O-alk or —CO—$NH_2$, $R_{26}$ represents an alkyl, $Ar_1$ or $Het_1$ radical, $Ar_1$ represents a phenyl, naphthyl or indenyl radical, these radicals optionally being substituted by one or more halogen, alkyl, alkoxy, cyano, —CO-alk, —COOH, —COOalk, —$CONR_{27}R_{28}$, —CO—NH—$NR_{29}R_{30}$, alkylsulfanyl, alkylsulfinyl, alkylsulfonyl, -alk-$NR_{29}R_{30}$, —$NR_{29}R_{30}$, alkylthioalkyl, formyl, hydroxyl, hydroxyalkyl, Het, —O-alk-NH-cycloalkyl, $OCF_3$, $CF_3$, —NH—CO-alk, —$SO_2NH_2$, —NH—$COCH_3$, —NH—COOalk or Het or else on 2 adjacent carbon atoms by dioxymethylene, $Het_1$ represents an unsaturated or saturated mono- or bicyclic heterocycle having 3 to 10 ring members and comprising one or more heteroatoms chosen from oxygen, sulfur and nitrogen which is optionally substituted by one or more alkyl, alkoxy, vinyl, halogen, alkoxycarbonyl, oxo, hydroxyl, $OCF_3$ or $CF_3$, the nitrogenous heterocycles optionally being in their N-oxidized form, $R_{27}$ and $R_{28}$, which are identical or different, represent a hydrogen atom or an alkyl radical or else $R_{27}$ and $R_{28}$ form, together with the nitrogen atom to which they are attached, a saturated mono- or bicyclic heterocycle having 3 to 10 ring members optionally comprising another heteroatom chosen from oxygen, sulfur and nitrogen and optionally being substituted by one or more alkyl radicals, $R_{29}$ and $R_{30}$, which are identical or different, represent a hydrogen atom or an alkyl, —COOalk, cycloalkyl, alkylcycloalkyl, -alk-O-alk or hydroxyalkyl radical or else $R_{29}$ and $R_{30}$ form, together with the nitrogen atom to which they are attached, a saturated or unsaturated mono- or bicyclic heterocycle having 3 to 10 ring members optionally comprising another heteroatom chosen from oxygen, sulfur and nitrogen and optionally being substituted by one or more alkyl, —COalk, —COOalk, —CO—NHalk, —CS—NHalk, oxo, hydroxyalkyl, -alk-O-alk or —CO—$NH_2$ radicals, or R represents $CHR_{31}$ and $R_{31}$ represents an —$N(R_{32})R_{33}$, —$N(R_{32})$—CO—$R_{33}$ or —$N(R_{32})$—$SO_2R_{34}$ radical, $R_4$ and $R_3$, which are identical or different, represent either an aromatic chosen from phenyl, naphthyl and indenyl, these aromatics being unsubstituted or substituted by one or more halogen, alkyl, alkoxy, formyl, hydroxyl, trifluoromethyl, trifluoromethoxy, —CO-alk, cyano, —COOH, COOalk, —$CONR_{22}R_{23}$, —CO—NH—$NR_{24}R_{25}$, alkylsulfanyl, alkylsulfinyl, alkylsulfonyl, alkylsulfanylalkyl, alkylsulfinylalkyl, alkylsulfonylalkyl, hydroxyalkyl or -alk-$NR_7R_8$, or a heteroaromatic chosen from the benzofuryl, benzothiazolyl, benzothienyl, benzoxazolyl, chromanyl, 2,3-dihydrobenzofuryl, 2,3-dihydrobenzothienyl, furyl, imidazolyl, isochromanyl, isoquinolyl, pyrrolyl, pyridyl, pyrimidyl, quinolyl, 1,2,3,4-tetrahydroisoquinolyl, thiazolyl and thienyl rings, it being possible for these heteroaromatics to be unsubstituted or substituted by a halogen, alkyl, alkoxy, hydroxyl, trifluoromethyl, trifluoromethoxy, cyano, —COOH, —COOalk, —CO—NH—$NR_{24}R_{25}$, —$CONR_{22}R_{23}$, -alk-$NR_{24}R_{25}$, alkylsulfanyl, alkylsulfinyl, alkylsulfonyl, alkylsulfanylalkyl, alkylsulfinylalkyl, alkylsulfonylalkyl or hydroxyalkyl, $R_{32}$ represents a —$C(R_{35})(R_{36})$-$Het_2$, -$Het_2$, —$C(R_{35})(R_{36})$—$Ar_2$, $Ar_2$, cycloalkyl or norbornyl radical, $R_{33}$ represents a hydrogen atom or a hydroxyalkyl, -alk-COOalk, -alk-$CONR_{22}R_{23}$, -alk-$NR_{22}R_{23}$, alkoxy, $Ar_2$, $Het_2$, —$CH_2Ar_2$, —$CH_2Het_2$ or alkyl radical, the latter optionally substituted by one or more halogen, $R_{34}$ represents a hydroxyalkyl, -alk-COOalk, -alk-$CONR_{22}R_{23}$, -alk-$NR_{22}R_{23}$, alkoxy, $Ar_2$, $Het_2$, —$CH_2Ar_2$, —$CH_2Het_2$ or alkyl radical, the latter optionally substituted by one or more halogen, $R_{35}$ represents a hydrogen atom or a hydroxyalkyl, -alk-COOalk, -alk-$CONR_{22}R_{23}$, -alk-$NR_{22}R_{23}$, alkoxyalkyl, $Ar_2$, $Het_2$, —$CH_2Ar_2$, —$CH_2Het_2$ or alkyl radical, the latter optionally substituted by one or more halogen, R₃₆ represents a hydrogen atom or a hydroxyalkyl, -alk-COOalk, -alk-CONR₂₂R₂₃, -alk-NR₂₂R₂₃, alkoxyalkyl or alkyl radical, the latter optionally substituted by one or more halogen, or else R₃₅ and R₃₆ form, together with the carbon atom to which they are attached, a saturated mono- or bicyclic ring having 3 to 10 ring members optionally comprising another heteroatom chosen from oxygen, sulfur and nitrogen and optionally being substituted by one or more alkyl, Ar₂ represents a phenyl, naphthyl or indenyl radical, these various radicals optionally being substituted by one or more halogen, alkyl, alkoxy, —CO-alk, cyano, —COOH, —COOalk, —CONR₃₇R₃₈, —CO—NH—R₃₉R₄₀, alkylsulfanyl, alkylsulfinyl, alkylsulfonyl, -alk-NR₃₉R₄₀, —NR₃₉R₄₀, alkylthioalkyl, formyl, CF₃, OCF₃, Het, —O-alk-NH-cycloalkyl, SO₂NH₂, hydroxyl, hydroxyalkyl, —NHCOalk or NHCOOalk or on 2 adjacent carbon atoms by dioxymethylene, Het₂ represents an unsaturated or saturated mono- or bicyclic heterocycle having 3 to 10 ring members and comprising one or more heteroatoms chosen from oxygen, sulfur and nitrogen which is optionally substituted by one or more alkyl, alkoxy, halogen, alkoxycarbonyl, oxo or hydroxyl, the nitrogenous heterocycles optionally being in their N-oxidized form, R₃₇ and R₃₈, which are identical or different, represent a hydrogen atom or an alkyl radical or else R₃₇ and R₃₈ form, together with the nitrogen atom to which they are attached, a saturated mono- or bicyclic heterocycle having 3 to 10 ring members optionally comprising another heteroatom chosen from oxygen, sulfur and nitrogen and optionally being substituted by one or more alkyl, R₃₉ and R₄₀, which are identical or different, represent a hydrogen atom or an alkyl radical or else R₃₉ and R₄₀ form, together with the nitrogen atom to which they are attached, a saturated mono- or bicyclic heterocycle having 3 to 10 ring members optionally comprising another heteroatom chosen from oxygen, sulfur and nitrogen and optionally being substituted by one or more alkyl, alk represents an alkyl or alkylene radical, the alkyl and alkylene radicals and portions and the alkoxy radicals and portions have straight or branched chains and comprise 1 to 6 carbon atoms and the cycloalkyl radicals comprise 3 to 10 carbon atoms, the optical isomers of these compounds and their pharmaceutically acceptable salts with an inorganic or organic acid.

The preferred azetidine derivatives are as follows:

1-benzhydryl-3-[(methylsulfonyl)(phenyl)methylene]azetidine,
1-benzhydryl-3-[(3-methylphenyl)(methylsulfonyl)methylene]azetidine,
1-benzhydryl-3-[(3-chlorophenyl)(methylsulfonyl)methylene]azetidine,
1-benzhydryl-3-[(3,5-dichlorophenyl)(methylsulfonyl)methylene]azetidine,
1-benzhydryl-3-[(2,5-dichlorophenyl)(methylsulfonyl)methylene]azetidine,
1-benzhydryl-3-[(2,3-dichlorophenyl)(methylsulfonyl)methylene]azetidine,
1-benzhydryl-3-[(3-fluorophenyl)(methylsulfonyl)methylene]azetidine,
1-benzhydryl-3-[(3,5-difluorophenyl)(methylsulfonyl)methylene]azetidine,
1-benzhydryl-3-[(3-bromophenyl)(methylsulfonyl)methylene]azetidine,
1-benzhydryl-3-[(3-iodophenyl)(methylsulfonyl)methylene]azetidine,
1-benzhydryl-3-[(methylsulfonyl)(3-trifluoromethoxyphenyl)methylene]azetidine,
1-benzhydryl-3-[(methylsulfonyl)(3-trifluoromethylphenyl)methylene]azetidine,
1-benzhydryl-3-{[3,5-bis(trifluoromethyl)phenyl](methylsulfonyl)methylene}azetidine,
1-benzhydryl-3-[(3,5-dibromophenyl)(methylsulfonyl)methylene]azetidine,
1-benzhydryl-3-[(3-methoxycarbonylphenyl)(methylsulfonyl)methylene]azetidine,
1-benzhydryl-3-[(3-cyanophenyl)(methylsulfonyl)methylene]azetidine,
1-benzhydryl-3-[(3-carbamoylphenyl)(methylsulfonyl)methylene]azetidine,
1-benzhydryl-3-[(methylsulfonyl)(naphth-1-yl)(methylsulfonyl)methylene]azetidine,
1-[bis(4-chlorophenyl)methyl]-3-[(3,5-difluorophenyl)(methylsulfonyl)methylene]azetidine,
1-[bis(4-methoxyphenyl)methyl]-3-[(3,5-difluorophenyl)(methylsulfonyl)methylene]azetidine,
1-[bis(4-methylphenyl)methyl]-3-[(3,5-difluorophenyl)(methylsulfonyl)methylene]azetidine,
(RS)-3-[(3,5-difluorophenyl)(methylsulfonyl)methylene]-1-[(4-methoxyphenyl)(phenyl)methyl]azetidine,
(R)-3-[(3,5-difluorophenyl)(methylsulfonyl)methylene]-1-[(4-methoxyphenyl)(phenyl)methyl]azetidine,
(S)-3-[(3,5-difluorophenyl)(methylsulfonyl)methylene]-1-[(4-methoxyphenyl)(phenyl)methyl]azetidine,
1-[bis(4-trifluoromethoxyphenyl)methyl]-3-[(3,5-difluorophenyl)(methylsulfonyl)methylene]azetidine,
1-[bis(4-trifluoromethylphenyl)methyl]-3-[(3,5-difluorophenyl)(methylsulfonyl)methylene]azetidine,
1-[bis(4-chlorophenyl)methyl]-3-{[3,5-bis(trifluoromethyl)phenyl]methylsulfonylmethylene}azetidine,
(RS)-1-[(4-chlorophenyl)(2,4-dichlorophenyl)methyl]-3-[(3,5-difluorophenyl)(methylsulfonyl)methylene]azetidine,
(R)-1-[(4-chlorophenyl)(2,4-dichlorophenyl)methyl]-3-[(3,5-difluorophenyl)(methylsulfonyl)methylene]azetidine,
(S)-1-[(4-chlorophenyl)(2,4-dichlorophenyl)methyl]-3-[(3,5-difluorophenyl)(methylsulfonyl)methylene]azetidine,
(RS)-1-{(4-chlorophenyl)[4-(hydroxymethyl)phenyl]methyl}-3-[(3,5-difluorophenyl)(methylsulfonyl)methylene]azetidine,
(R)-1-{(4-chlorophenyl)[4-(hydroxymethyl)phenyl]methyl}-3-[(3,5-difluorophenyl)(methylsulfonyl)methylene]azetidine,
(S)-1-{(4-chlorophenyl)[4-(hydroxymethyl)phenyl]methyl}-3-[(3,5-difluorophenyl)(methylsulfonyl)methylene]azetidine,
(RS)-1-{(4-chlorophenyl)[4-(pyrrolidylmethyl)phenyl]methyl}-3-[(3,5-difluorophenyl)(methylsulfonyl)methylene]azetidine,
(R)-1-{(4-chlorophenyl)[4-(pyrrolidylmethyl)phenyl]methyl}-3-[(3,5-difluorophenyl)(methylsulfonyl)methylene]azetidine,
(S)-1-{(4-chlorophenyl)[4-(pyrrolidylmethyl)phenyl]methyl}-3-[(3,5-difluorophenyl)(methylsulfonyl)methylene]azetidine,
1-{(RS)-(4-chlorophenyl)[4-(3,3-dimethylpiperidin-1-ylmethyl)phenyl]methyl}-3-[(3,5-difluorophenyl)(methylsulfonyl)methylene]azetidine,
1-{(R)-(4-chlorophenyl)[4-(3,3-dimethylpiperidin-1-ylmethyl)phenyl]methyl}-3-[(3,5-difluorophenyl)(methylsulfonyl)methylene]azetidine, 1-{(S)-(4-chlorophenyl)[4-(3,3-dimethylpiperidin-1-ylmethyl)phenyl]methyl}-3-[(3,5-difluorophenyl)(methylsulfonyl)methylene]azetidine, 1-{(RS)-(4-chlorophenyl)[4-(thiomorpholin-4-ylmethyl)phenyl]methyl}-3-[(3,5-difluorophenyl)(methylsulfonyl)methylene]azetidine, 1-{(R)-(4-chlorophenyl)[4-(thiomorpholin-4-ylmethyl)phenyl]methyl}-3-[(3,5-difluorophenyl)(methylsulfonyl)methylene]azetidine, 1-{(S)-(4-chlorophenyl)[4-(thiomorpholin-4-ylmethyl)phenyl]methyl}-3-[(3,5-difluorophenyl)(methylsulfonyl)methylene]azetidine, 1-{(RS)-(4-chlorophenyl)[4-(N-ethyl-N-cyclohexylaminomethyl)phenyl]methyl}-3-[(3,5-difluorophenyl)(methylsulfonyl)methylene]azetidine, 1-{(R)-(4-chlorophenyl)[4-(N-ethyl-N-cyclohexylaminomethyl)phenyl]methyl}-3-[(3,5-difluorophenyl)(methylsulfonyl)methylene]azetidine, 1-{(S)-(4-chlorophenyl)[4-(N-ethyl-N-cyclohexylaminomethyl)phenyl]methyl}-3-[(3,5-difluorophenyl)(methylsulfonyl)methylene]azetidine, 1-{{(RS)-(4-chlorophenyl){4-[(4-ethoxycarbonylpiperazinyl)methyl]phenyl}methyl}}-3-[(3,5-difluorophenyl)(methylsulfonyl)methylene]azetidine, 1-{{(R)-(4-chlorophenyl){4-[(4-ethoxycarbonylpiperazinyl)methyl]phenyl}methyl}}-3-[(3,5-difluorophenyl)(methylsulfonyl)methylene]azetidine, 1-{{(S)-(4-chlorophenyl){4-[(4-ethoxycarbonylpiperazinyl)methyl]phenyl}methyl}}-3-[(3,5-difluorophenyl)(methylsulfonyl)methylene]azetidine, 1-{(RS)-(4-chlorophenyl)[4-(N-cyclopropyl-N-propylaminomethyl)phenyl]methyl}-3-[(3,5-difluorophenyl)(methylsulfonyl)methylene]azetidine, 1-{(R)-(4-chlorophenyl)[4-(N-cyclopropyl-N-propylaminomethyl)phenyl]methyl}-3-[(3,5-difluorophenyl)(methylsulfonyl)methylene]azetidine, 1-{(S)-(4-chlorophenyl)[4-(N-cyclopropyl-N-propylaminomethyl)phenyl]methyl}-3-[(3,5-difluorophenyl)(methylsulfonyl)methylene]azetidine, 1-{(RS)-(4-chlorophenyl)[4-(diisopropylaminomethyl)phenyl]methyl}-3-[(3,5-difluorophenyl)(methylsulfonyl)methylene]azetidine, 1-{(R)-(4-chlorophenyl)[4-(diisopropylaminomethyl)phenyl]methyl}-3-[(3,5-difluorophenyl)(methylsulfonyl)methylene]azetidine, 1-{(S)-(4-chlorophenyl)[4-(diisopropylaminomethyl)phenyl]methyl}-3-[(3,5-difluorophenyl)(methylsulfonyl)methylene]azetidine, 1-{{(RS)-(4-chlorophenyl){4-[bis(2-methoxyethyl)aminomethyl]phenyl}methyl}}-3-[(3,5-difluorophenyl)(methylsulfonyl)methylene]azetidine, 1-{{(R)-(4-chlorophenyl){4-[bis(2-methoxyethyl)aminomethyl]phenyl}methyl}}-3-[(3,5-difluorophenyl)(methylsulfonyl)methylene]azetidine, 1-{{(S)-(4-chlorophenyl){4-[bis(2-methoxyethyl)aminomethyl]phenyl}methyl}}-3-[(3,5-difluorophenyl)(methylsulfonyl)methylene]azetidine, 1-{(RS)-(4-chlorophenyl)[4-[di-n-propylaminomethyl)phenyl]methyl}-3-[(3,5-difluorophenyl)(methylsulfonyl)methylene]azetidine, 1-{(R)-(4-chlorophenyl)[4-(di-n-propylaminomethyl)phenyl]methyl}-3-[(3,5-difluorophenyl)(methylsulfonyl)methylene]azetidine, 1-{(S)-(4-chlorophenyl)[4-(di-n-propylaminomethyl)phenyl]methyl}-3-[(3,5-difluorophenyl)(methylsulfonyl)methylene]azetidine, 1-{(RS)-(4-chlorophenyl)[4-(piperidin-1-ylmethyl)phenyl]methyl}-3-[(3,5-difluorophenyl)(methylsulfonyl)methylene]azetidine, 1-{(R)-(4-chlorophenyl)[4-(piperidin-1-ylmethyl)phenyl]methyl}-3-[(3,5-difluorophenyl)(methylsulfonyl)methylene]azetidine, 1-{(S)-(4-chlorophenyl)[4-(piperidin-1-ylmethyl)phenyl]methyl}-3-[(3,5-difluorophenyl)(methylsulfonyl)methylene]azetidine, 1-{(RS)-(4-chlorophenyl)[4-(4-methylpiperazin-1-ylmethyl)phenyl]methyl}-3-[(3,5-difluorophenyl)(methylsulfonyl)methylene]azetidine, 1-{(R)-(4-chlorophenyl)[4-(4-methylpiperazin-1-ylmethyl)phenyl]methyl}-3-[(3,5-difluorophenyl)(methylsulfonyl)methylene]azetidine, 1-{(S)-(4-chlorophenyl)[4-(4-methylpiperazin-1-ylmethyl)phenyl]methyl}-3-[(3,5-difluorophenyl)(methylsulfonyl)methylene]azetidine, 1-{(RS)-(4-chlorophenyl)[4-(morpholin-4-ylmethyl)phenyl]methyl}-3-[(3,5-difluorophenyl)(methylsulfonyl)methylene]azetidine, 1-{(R)-(4-chlorophenyl)[4-(morpholin-4-ylmethyl)phenyl]methyl}-3-[(3,5-difluorophenyl)(methylsulfonyl)methylene]azetidine, 1-{(S)-(4-chlorophenyl)[4-(morpholin-4-ylmethyl)phenyl]methyl}-3-[(3,5-difluorophenyl)(methylsulfonyl)methylene]azetidine, 1-{(RS)-(4-chlorophenyl)[4-(diethylaminomethyl)phenyl]methyl}-3-[(3,5-difluorophenyl)(methylsulfonyl)methylene]azetidine, 1-{(R)-(4-chlorophenyl)[4-(diethylaminomethyl)phenyl]methyl}-3-[(3,5-difluorophenyl)(methylsulfonyl)methylene]azetidine, 1-{(S)-(4-chlorophenyl)[4-(diethylaminomethyl)phenyl]methyl}-3-[(3,5-difluorophenyl)(methylsulfonyl)methylene]azetidine, 1-{(RS)-(4-chlorophenyl)[4-(piperazin-2-one-4-ylmethyl)phenyl]methyl}-3-[(3,5-difluorophenyl)(methylsulfonyl)methylene]azetidine, 1-{(R)-(4-chlorophenyl)[4-(piperazin-2-one-4-ylmethyl)phenyl]methyl}-3-[(3,5-difluorophenyl)(methylsulfonyl)methylene]azetidine, 1-{(S)-(4-chlorophenyl)[4-(piperazin-2-one-4-ylmethyl)phenyl]methyl}-3-[(3,5-difluorophenyl)(methylsulfonyl)methylene]azetidine, 1-{(RS)-(4-chlorophenyl)[4-(imidazol-1-ylmethyl)phenyl]methyl}-3-[(3,5-difluorophenyl)(methylsulfonyl)methylene]azetidine, 1-{(R)-(4-chlorophenyl)[4-(imidazol-1-ylmethyl)phenyl]methyl}-3-[(3,5-difluorophenyl)(methylsulfonyl)methylene]azetidine, 1-{(S)-(4-chlorophenyl)[4-(imidazol-1-ylmethyl)phenyl]methyl}-3-[(3,5-difluorophenyl)(methylsulfonyl)methylene]azetidine, (RS)-1-{(4-chlorophenyl)[4-(N,N-dimethylcarbamoyl)phenyl]methyl}-3-[(3,5-difluorophenyl)(methylsulfonyl)methylene]azetidine, (R)-1-{(4-chlorophenyl)[4-(N,N-dimethylcarbamoyl)phenyl]methyl}-3-[(3,5-difluorophenyl)(methylsulfonyl)methylene]azetidine, (S)-1-{(4-chlorophenyl)[4-(N,N-dimethylcarbamoyl)phenyl]methyl}-3-[(3,5-difluorophenyl)(methylsulfonyl)methylene]azetidine, (RS)-1-{(4-chlorophenyl)[4-(N-ethylcarbamoyl)phenyl]methyl)}-3-[(3,5-difluorophenyl)(methylsulfonyl)methylene]azetidine, (R)-1-{(4-chlorophenyl)[4-(N-ethylcarbamoyl)phenyl]methyl}-3-[(3,5-difluorophenyl)(methylsulfonyl)methylene]azetidine,
(S)-1-{(4-chlorophenyl)[4-(N-ethylcarbamoyl)phenyl]methyl}-3-[(3,5-difluorophenyl)(methylsulfonyl)methylene]azetidine,
(RS)-1-[(4-carbamoylphenyl)(4-chlorophenyl)methyl]-3-[(3,5-difluorophenyl)(methylsulfonyl)methylene]azetidine,
(R)-1-[(4-carbamoylphenyl)(4-chlorophenyl)methyl]-3-[(3,5-difluorophenyl)(methylsulfonyl)methylene]azetidine,
(S)-1-[(4-carbamoylphenyl)(4-chlorophenyl)methyl]-3-[(3,5-difluorophenyl)(methylsulfonyl)methylene]azetidine,
1-[bis(4-chlorophenyl)methyl]-3-[(3,5-dichlorophenyl)(methylsulfonyl)methylene]azetidine,
1-benzhydryl-3-[(3-methylsulfanylphenyl)(methylsulfonyl)methylene]azetidine,
1-benzhydryl-3-[(3-methylsulfanylmethyl)phenyl)](methylsulfonyl)methylene]azetidine,
1-[bis(4-chlorophenyl)methyl]-3-[(3-cyanophenyl)(methylsulfonyl)methylene]azetidine,
1-[bis(4-chlorophenyl)methyl]-3-[(3-carbamoylphenyl)(methylsulfonyl)methylene]azetidine,
1-[bis(4-chlorophenyl)methyl]-3-[(3-methoxyphenyl)(methylsulfonyl)methylene]azetidine,
1-[bis(4-chlorophenyl)methyl]-3-[(3-hydroxyphenyl)(methylsulfonyl)methylene]azetidine,
1-[bis(4-chlorophenyl)methyl]-3-[(methylsulfonyl)(3-pyrrolidinylphenyl)methylene]azetidine,
1-[bis(4-chlorophenyl)methyl]-3-[(3-hydroxymethylphenyl)(methylsulfonyl)methylene]azetidine,
1-[bis(4-chlorophenyl)methyl]-3-{(methylsulfonyl)[3-(N-piperidylcarbamoyl)phenyl]methylene}azetidine,
1-[bis(4-chlorophenyl)methyl]-3-[(methylsulfonyl)(3-trifluoromethylsulfanylphenyl)(methylsulfonyl)methylene]azetidine,
1-[bis(4-fluorophenyl)methyl]-3-[(3,5-difluorophenyl)(methylsulfonyl)methylene]azetidine,
1-[bis(2-fluorophenyl)methyl]-3-[(3,5-difluorophenyl)(methylsulfonyl)methylene]azetidine,
1-[bis(3-fluorophenyl)methyl]-3-[(3,5-difluorophenyl)(methylsulfonyl)methylene]azetidine,
(RS)-1-[(4-chlorophenyl)(thiazol-2-yl)methyl]-3-[(methylsulfonyl)(phenyl)methylene]azetidine,
(R)-1-[(4-chlorophenyl)(thiazol-2-yl)methyl]-3-[(methylsulfonyl)(phenyl)methylene]azetidine,
(S)-1-[(4-chlorophenyl)(thiazol-2-yl)methyl]-3-[(methylsulfonyl)(phenyl)methylene]azetidine,
(RS)-1-[(4-chlorophenyl)(thien-2-yl)methyl]-3-[(3,5-difluorophenyl)(methylsulfonyl)methylene]azetidine,
(R)-1-[(4-chlorophenyl)(thien-2-yl)methyl]-3-[(3,5-difluorophenyl)(methylsulfonyl)methylene]azetidine,
(S)-1-[(4-chlorophenyl)(thien-2-yl)methyl]-3-[(3,5-difluorophenyl)(methylsulfonyl)methylene]azetidine,
1-benzhydryl-3-[(ethylsulfonyl)(phenyl)methylene]azetidine,
1-[bis(4-chlorophenyl)methyl]-3-{{3-[N-(4-methylpiperazinyl)carbamoyl]phenyl}(methylsulfonyl)methylene}azetidine,
1-[bis(4-chlorophenyl)methyl]-3-{[3-(2,2-dimethylcarbohydrazido)phenyl](methylsulfonyl)methylene}azetidine,
1-[bis(thien-2-yl)methyl]-3-[(3,5-difluorophenyl)(methylsulfonyl)methylene]azetidine,
1-[bis(p-tolyl)methyl]-3-[(methylsulfonyl)(phenyl)methylene]azetidine,
1-[(4-chlorophenyl)(4-hydroxymethylphenyl)methyl]-3-[(3,5-difluorophenyl)(methylsulfonyl)methylene]azetidine,
1-[bis(4-chlorophenyl)methyl]-3-[(3-methylaminophenyl)(methylsulfonyl)methylene]azetidine,
(RS)-1-[(4-chlorophenyl)(thiazol-2-yl)methyl]-3-[(3,5-difluorophenyl)(methylsulfonyl)methylene]azetidine,
(R)-1-[(4-chlorophenyl)(thiazol-2-yl)methyl]-3-[(3,5-difluorophenyl)(methylsulfonyl)methylene]azetidine,
(S)-1-[(4-chlorophenyl)(thiazol-2-yl)methyl]-3-[(3,5-difluorophenyl)(methylsulfonyl)methylene]azetidine,
1-[bis(4-chlorophenyl)methyl]-3-[(methylsulfonyl)(2-methoxycarbonylthien-5-yl)methylene]azetidine,
(RS)-1-[bis(4-chlorophenyl)methyl]-3-hydroxy-3-[(methylsulfonyl)(2-methoxycarbonylthien-5-yl)methyl]azetidine,
1-[bis(4-chlorophenyl)methyl]-3-[(2-isobutylaminocarbonylthien-5-yl)(methylsulfonyl)methylene]azetidine,
1-[bis(4-chlorophenyl)methyl]-3-[(RS)-(3-methoxycarbonylphenyl)(methylsulfonyl)methyl]azetidin-3-ol,
1-[bis(4-chlorophenyl)methyl]-3-[(RS)-(methylsulfonyl)(pyridin-4-yl)methyl]azetidin-3-ol,
1-[bis(4-chlorophenyl)methyl]-3-[(RS)-(methylsulfonyl)(pyridin-3-yl)methyl]azetidin-3-ol,
3-({1-[bis(4-chlorophenyl)methyl]azetidin-3-ylidene}(methanesulfonyl)methyl)-N-(3-(morpholin-4-yl)propyl)benzamide,
3-({1-[bis(4-chlorophenyl)methyl]azetidin-3-ylidene}(methanesulfonyl)methyl)-N-(3-dimethylaminopropyl)benzamide,
3-({1-[bis(4-chlorophenyl)methyl]azetidin-3-ylidene}(methanesulfonyl)methyl)-N-(2-(pyrrolidin-1-yl)ethyl)benzamide,
3-({1-[bis(4-chlorophenyl)methyl]azetidin-3-ylidene}(methanesulfonyl)methyl)-N-(2-dimethylamino-1-methylethyl)benzamide,
3-({1-[bis(4-chlorophenyl)methyl]azetidin-3-ylidene}(methanesulfonyl)methyl)-N-(piperidin-1-yl)benzamide,
3-({1-[bis(4-chlorophenyl)methyl]azetidin-3-ylidene}(methanesulfonyl)methyl)-N-isobutylbenzamide,
3-({1-[bis(4-chlorophenyl)methyl]azetidin-3-ylidene}(methanesulfonyl)methyl)-N-(3-(imidazol-1-yl)propyl)benzamide,
3-({1-[bis(4-chlorophenyl)methyl]azetidin-3-ylidene}(methanesulfonyl)methyl)-N-(2-dimethylaminoethyl)benzamide,
N'-methylhydrazide of 3-({1-[bis(4-chlorophenyl)methyl]azetidin-3-ylidene}(methanesulfonyl)methyl)benzoic acid,
3-({1-[bis(4-chlorophenyl)methyl]azetidin-3-ylidene}(methanesulfonyl)methyl)-N-(2-(morpholin-4-yl)ethyl)benzamide,
3-({1-[bis(4-chlorophenyl)methyl]azetidin-3-ylidene}(methanesulfonyl)methyl)-N-(1-ethylpyrrolidin-2-ylmethyl)benzamide,
3-({1-[bis(4-chlorophenyl)methyl]azetidin-3-ylidene}(methanesulfonyl)methyl)-N-(2,2-dimethylpropyl)benzamide,
3-({1-[bis(4-chlorophenyl)methyl]azetidin-3-ylidene}(methanesulfonyl)methyl)-N-(cyclohexylmethyl)benzamide,
3-({1-[bis(4-chlorophenyl)methyl]azetidin-3-ylidene}(methanesulfonyl)methyl)-N-(cyclopropylmethyl)benzamide,
3-({1-[bis(4-chlorophenyl)methyl]azetidin-3-ylidene}(methanesulfonyl)methyl)-N-(2-methylbutyl)benzamide,
3-({1-[bis(4-chlorophenyl)methyl]azetidin-3-ylidene}(methanesulfonyl)methyl)-N-(2-phenylpropyl)benzamide, 3-({1-[bis(4-chlorophenyl)methyl]azetidin-3-ylidene} (methanesulfonyl)methyl)-N-(tetrahydrofuran-2-ylmethyl)benzamide,
3-({1-[bis(4-chlorophenyl)methyl]azetidin-3-ylidene} (methanesulfonyl)methyl)-N-(2,2-diphenylethyl)benzamide,
3-({1-[bis(4-chlorophenyl)methyl]azetidin-3-ylidene} (methanesulfonyl)methyl)-N-(2-ethylbutyl)benzamide,
methyl ester of 4-{[3-({1-[bis(4-chlorophenyl)methyl]azetidin-3-ylidene}(methanesulfonyl)methyl)benzoylamino]methyl}cyclohexanecarboxylic acid,
2-amino-1-{4-[3-({1-[bis(4-chlorophenyl)methyl]azetidin-3-ylidene}(methanesulfonyl)methyl)phenyl]piperazin-1-yl}ethanone,
tert-butyl ester of (2-{4-[3-({1-[bis(4-chlorophenyl)methyl]azetidin-3-ylidene}(methanesulfonyl)methyl)phenyl]piperazin-1-yl}-2-oxoethyl)carbamic acid,
1-{4-[3-({1-[bis(4-chlorophenyl)methyl]azetidin-3-ylidene}(methanesulfonyl)methyl)phenyl]piperazin-1-yl}-2-(methylamino)ethanone,
tert-butyl ester of (2-{4-[3-({1-[bis(4-chlorophenyl)methyl]azetidin-3-ylidene}(methanesulfonyl)methyl)phenyl]piperazin-1-yl}-2-oxoethyl)-N-methylcarbamic acid,
N-methylamide of 4-[3-({1-[bis(4-chlorophenyl)methyl]azetidin-3-ylidene}(methanesulfonyl)methyl)phenyl]piperazine-1-carbothioic acid,
N-methylamide of 4-[3-({1-[bis(4-chlorophenyl)methyl]azetidin-3-ylidene}(methanesulfonyl)methyl)phenyl]piperazine-1-carboxylic acid,
methyl ester of 4-[3-({1-[bis(4-chlorophenyl)methyl]azetidin-3-ylidene}(methanesulfonyl)methyl)-phenyl]piperazine-1-carboxylic acid,
1-[3-({1-[bis(4-chlorophenyl)methyl]azetidin-3-ylidene} (methanesulfonyl)methyl)phenyl]-4-isobutylpiperazine,
1-[3-({1-[bis(4-chlorophenyl)methyl]azetidin-3-ylidene} (methanesulfonyl)methyl)phenyl]-4-ethylpiperazine,
4-acetyl-1-[3-({1-[bis(4-chlorophenyl)methyl]azetidin-3-ylidene}(methanesulfonyl)methyl)phenyl]piperazine,
1-{4-[3-({1-[bis(4-chlorophenyl)methyl]azetidin-3-ylidene}(methanesulfonyl)methyl)phenyl]piperazin-1-yl}-2-dimethylaminoethanone,
1-[3-({1-[bis(4-chlorophenyl)methyl]azetidin-3-ylidene} (methanesulfonyl)methyl)phenyl]piperazine,
tert-butyl ester of 4-[3-({1-[bis(4-chlorophenyl)methyl]azetidin-3-ylidene}(methanesulfonyl)methyl)-phenyl]piperazine-1-carboxylic acid,
1-[bis(4-methoxycarbonylphenyl)methyl]-3-[(3,5-difluorophenyl)(methylsulfonyl)methylene]azetidine,
3-acetoxy-1-[bis(4-methoxycarbonylphenyl)methyl]-3-[(RS)-(3,5-difluorophenyl)(methylsulfonyl)methyl]azetidine,
(RS)-4-[4-((4-chlorophenyl){3-[(3,5-difluorophenyl)(methanesulfonyl)methylene]azetidin-1-yl}methyl)benzyl]morpholine,
4-(4-{3-[(1-benzhydrylazetidin-3-ylidene)(methanesulfonyl)methyl]phenoxy}butyl)morpholine,
4-(4-{3-[(1-benzhydrylazetidin-3-ylidene)(methanesulfonyl)methyl]phenoxy}propyl)morpholine,
N-{1-[bis(4-chlorophenyl)methyl]azetidin-3-yl}thien-2-ylsulfonamide,
N-{1-[bis(4-chlorophenyl)methyl]azetidin-3-yl}-4-methoxyphenylsulfonamide,
N-[4-(N-{1-[bis(4-chlorophenyl)methyl]azetidin-3-yl}sulfamoyl)phenyl]acetamide,
N-{1-[bis(4-chlorophenyl)methyl]azetidin-3-yl}-4-methylphenylsulfonamide,
N-{1-[bis(4-chlorophenyl)methyl]azetidin-3-yl}-3,4-dimethoxyphenylsulfonamide,
N-{1-[bis(4-chlorophenyl)methyl]azetidin-3-yl}-3-fluorophenylsulfonamide,
N-{1-[bis(4-chlorophenyl)methyl]azetidin-3-yl}-3,4-dichlorophenylsulfonamide,
N-{1-[bis(4-chlorophenyl)methyl]azetidin-3-yl}-3-cyanophenylsulfonamide,
N-{1-[bis(4-chlorophenyl)methyl]azetidin-3-yl}-2,5-dimethoxyphenylsulfonamide,
N-{1-[bis(4-chlorophenyl)methyl]azetidin-3-yl}-3-trifluoromethylphenylsulfonamide,
N-{1-[bis(4-chlorophenyl)methyl]azetidin-3-yl}naphth-2-ylsulfonamide,
N-{1-[bis(4-chlorophenyl)methyl]azetidin-3-yl}naphth-1-ylsulfonamide,
N-{1-[bis(4-chlorophenyl)methyl]azetidin-3-yl}-3,4-difluorophenylsulfonamide,
N-{1-[bis(4-chlorophenyl)methyl]azetidin-3-yl}-1-methyl-1H-imidazol-4-ylsulfonamide,
N-[4-(N-{1-[bis(4-chlorophenyl)methyl]azetidin-3-yl}sulfamoyl)-2-chlorophenyl]acetamide,
N-{1-[bis(4-chlorophenyl)methyl]azetidin-3-yl}pyrid-3-ylsulfonamide,
N-{1-[bis(4-chlorophenyl)methyl]azetidin-3-yl}-4-fluorophenylsulfonamide,
N-{1-[bis(4-chlorophenyl)methyl]azetidin-3-yl}quinol-8-ylsulfonamide,
N-{1-[bis(4-chlorophenyl)methyl]azetidin-3-yl}phenylsulfonamide,
N-{1-[bis(4-chlorophenyl)methyl]azetidin-3-yl}(phenylmethyl)sulfonamide,
N-{1-[bis(4-chlorophenyl)methyl]azetidin-3-yl}-3,5-difluorophenylsulfonamide,
N-{1-[bis(4-chlorophenyl)methyl]azetidin-3-yl}pyrid-2-ylsulfonamide,
N-{1-[bis(4-chlorophenyl)methyl]azetidin-3-yl}(3-fluoro-5-pyrrolidin-1-ylphenyl)sulfonamide,
N-{1-[bis(4-chlorophenyl)methyl]azetidin-3-yl}-N-methyl-4-fluorophenylsulfonamide,
N-{1-[bis(4-chlorophenyl)methyl]azetidin-3-yl}-N-methylquinol-8-ylsulfonamide,
N-{1-[bis(4-chlorophenyl)methyl]azetidin-3-yl}-N-methylphenylsulfonamide,
N-{1-[bis(4-chlorophenyl)methyl]azetidin-3-yl}-N-methyl (phenylmethyl)sulfonamide,
N-{1-[bis(4-chlorophenyl)methyl]azetidin-3-yl}-3-sulfamoylphenylsulfonamide,
2-benzenesulfonyl-N-{1-[bis(4-chlorophenyl)methyl]azetidin-3-yl}acetamide,
N-{1-[bis(4-chlorophenyl)methyl]azetidin-3-yl}-2-(4-toluene-4-sulfonyl)acetamide,
(3-chloro-4-(methylsulfonyl)thiophene-2-carboxy){1-[bis(4-chlorophenyl)methyl]azetidin-3-yl]amide,
N-{1-[bis(4-chlorophenyl)methyl]azetidin-3-yl}-3-(2-phenylethylenesulfonyl)propionamide,
N-{1-[bis(4-chlorophenyl)methyl]azetidin-3-yl}-4-(methylsulfonyl)benzamide,
N-{1-[bis(4-chlorophenyl)methyl]azetidin-3-yl}-4-(methanesulfonyl)benzamide,
(5-(methylsulfonyl)thiophene-2-carboxy){1-[bis(4-chlorophenyl)methyl]azetidin-3-yl}amide,
(5-methylsulfonyl-3-methyl-4-vinylthiophene-2-carboxy) {1-[bis(4-chlorophenyl)methyl]azetidin-3-yl}amide,
(RS)-N-{1-[(4-chlorophenyl)(pyridin-3-yl)methyl]azetidin-3-yl}-3,5-difluorobenzenesulfonamide, (RS)-N-{1-[(4-chlorophenyl)(pyrimidin-5-yl)methyl]azetidin-3-yl}-3,5-difluorobenzenesulfonamide,
N-{1-[bis(4-chlorophenyl)methyl]azetidin-3-yl}-N-(6-chloropyrid-2-yl)methylsulfonamide,
N-{1-[bis(4-chlorophenyl)methyl]azetidin-3-yl}-N-(6-ethylpyrid-2-yl)methylsulfonamide,
N-{1-[bis(4-chlorophenyl)methyl]azetidin-3-yl}-N-(quinol-6-yl)methylsulfonamide,
N-{1-[bis(4-chlorophenyl)methyl]azetidin-3-yl}-N-(quinol-5-yl)methylsulfonamide,
N-{1-[bis(4-chlorophenyl)methyl]azetidin-3-yl}-N-(isoquinol-5-yl)methylsulfonamide,
N-{1-[bis(4-chlorophenyl)methyl]azetidin-3-yl}-N-(pyrid-3-yl)methylsulfonamide,
N-{1-[bis(4-chlorophenyl)methyl]azetidin-3-yl}-N-(pyrid-1-oxide-3-yl)methylsulfonamide,
N-(1R,2S,4S)-(bicyclo[2.2.1]hept-2-yl)-N-{1-[bis-(4-chlorophenyl)methyl]azetidin-3-yl}methylsulfonamide,
N-(1R,2R,4S)-(bicyclo[2.2.1]hept-2-yl)-N-{1-[bis-(4-chlorophenyl)methyl]azetidin-3-yl}methylsulfonamide,
N-{1-[bis(4-chlorophenyl)methyl]azetidin-3-yl}-N-(3,5-difluorophenyl)methylsulfonamide,
N-{1-[bis(4-chlorophenyl)methyl]azetidin-3-yl}-N-(thiazol-2-yl)methylsulfonamide,
N-{1-[bis(4-chlorophenyl)methyl]azetidin-3-yl}-N-(3-methoxyphenyl)methylsulfonamide,
N-{1-[bis(4-chlorophenyl)methyl]azetidin-3-yl}-N-(3-hydroxyphenyl)methylsulfonamide,
N-{1-[bis(4-chlorophenyl)methyl]azetidin-3-yl}-N-(3-(hydroxymethyl)phenyl)methylsulfonamide,
ethyl N-{1-[bis(4-chlorophenyl)methyl]azetidin-3-yl}-N-(methylsulfonyl)-3-aminobenzoate,
N-{1-[bis(4-chlorophenyl)methyl]azetidin-3-yl}-N-(isobutylpiperid-4-yl)methylsulfonamide,
N-benzyl-N-{1-[bis(4-chlorophenyl)methyl]azetidin-3-yl}amine,
N-{1-[bis(4-chlorophenyl)methyl]azetidin-3-yl}-N-(3,5-difluorobenzyl)amine,
N-{1-[bis(4-chlorophenyl)methyl]azetidin-3-yl}-N-(3,5-difluorobenzyl)methylsulfonamide,
N-{1-[bis(4-chlorophenyl)methyl]azetidin-3-yl}-N-(pyrid-3-ylmethyl)methylsulfonamide,
N-{1-[bis(4-fluorophenyl)methyl]azetidin-3-yl}-N-(3,5-difluorophenyl)methylsulfonamide,
(RS)-N-{1-[(4-chlorophenyl)(pyrid-3-yl)methyl]azetidin-3-yl}-N-(3,5-difluorophenyl)methylsulfonamide,
(R)-N-{1-[(4-chlorophenyl)(pyrid-3-yl)methyl]azetidin-3-yl}-N-(3,5-difluorophenyl)methylsulfonamide,
(S)-N-{1-[(4-chlorophenyl)(pyrid-3-yl)methyl]azetidin-3-yl}-N-(3,5-difluorophenyl)methylsulfonamide,
(RS)-N-{1-[(4-chlorophenyl)(pyrid-4-yl)methyl]azetidin-3-yl}-N-(3,5-difluorophenyl)methylsulfonamide,
(R)-N-{1-[(4-chlorophenyl)(pyrid-4-yl)methyl]azetidin-3-yl}-N-(3,5-difluorophenyl)methylsulfonamide,
(S)-N-{1-[(4-chlorophenyl)(pyrid-4-yl)methyl]azetidin-3-yl}-N-(3,5-difluorophenyl)methylsulfonamide,
(RS)-N-{1-[(4-chlorophenyl)(pyrimidin-5-yl)methyl]azetidin-3-yl}-N-(3,5-difluorophenyl)methylsulfonamide,
(R)-N-{1-[(4-chlorophenyl)(pyrimidin-5-yl)methyl]azetidin-3-yl}-N-(3,5-difluorophenyl)methylsulfonamide,
(S)-N-{1-[(4-chlorophenyl)(pyrimidin-5-yl)methyl]azetidin-3-yl}-N-(3,5-difluorophenyl)methylsulfonamide,
N-{1-[bis(4-chlorophenyl)methyl]azetidin-3-yl}-N-(3,5-difluorophenyl)benzylsulfonamide, their optical isomers and their pharmaceutically acceptable salts with an inorganic or organic acid.

And even more particularly preferred are the following azetidine derivatives:
1-[bis(4-chlorophenyl)methyl]-3-[(RS)-(3,5-difluorophenyl)(methylsulfonyl)methyl]azetidin-3-ol,
3-acetoxy-1-[bis(4-chlorophenyl)methyl]-3-[(RS)-(3,5-difluorophenyl)(methylsulfonyl)methyl]methylsulfonylmethyl]azetidine,
1-[bis(4-chlorophenyl)methyl]-3-[(3,5-difluorophenyl)(methylsulfonyl)methylene]azetidine, their optical isomers and their pharmaceutically acceptable salts with an inorganic or organic acid.

Mention may be made, as examples of pharmaceutically acceptable salts of the azetidine derivatives, of the following salts: benzenesulfonate, hydrobromide, hydrochloride, citrate, ethanesulfonate, fumarate, gluconate, iodate, isethionate, maleate, methanesulfonate, methylenebis-β-oxynaphthoate, nitrate, oxalate, pamoate, phosphate, salicylate, succinate, sulfate, tartrate, theophyllinacetate and p-toluenesulfonate.

Other CB1 receptor antagonists of use in the combinations according to the invention are, for example, the pyrazole derivatives disclosed in EP 576 357, EP 658 546, EP 656 354, WO 97/19063 and WO 00/46209, the benzothiophene and benzofuran derivatives disclosed in WO 96/02248 or the arylsulfonamides disclosed in WO 98/37061. Mention may in particular be made of the products known under the code SR141716 and LY320135.

The synergistic effect of the combination of sibutramine and of a CB1 receptor antagonist on food intake was determined according to the following protocol:

Obese Fa/fa Zucker rats aged 7 weeks and originating from Iffa-Credo, France, were used in this study. The rats are housed in individual cages and weighed every day between 8 and 10 o'clock in the morning. The amount of food is also weighed each morning at the same time. This food (M20, Pietrement, France) is changed every day and the rats have free access thereto for 24 hours. All the rats are treated for a week with the vehicle (miglyol 812N and 0.5% methylcellulose/0.2% polysorbate 80) in two consecutive administrations. The rats are treated from the 8th day with the vehicle, the CB1 receptor antagonist (1[bis(4-chlorophenyl)methyl]-3-[(3,5-difluorophenyl)(methylsulfonyl)methylene]azetidine) or sibutramine by the oral route (see table below).

The sibutramine is dissolved in a 0.5% methylcellulose/0.2% polysorbate 80 solution and administered at a dose of 3 mg/kg; the CB1 receptor antagonist is dissolved in miglyol 812N (Hüls, Germany) at a dose of 0.6 mg/kg and the two products are administered under a volume of 1 ml/kg. Each group is composed of 12 to 14 animals. The following groups are formed and the animals are treated for five days at the rate of two consecutive administrations every day.

| GROUP | First administration | Second administration |
|---|---|---|
| 1 "vehicle group" | miglyol | 0.5% methylcellulose/ 0.2% polysorbate |
| 2 "sibutramine group" | miglyol | sibutramine 3 mg/kg |
| 3 "CB1 receptor antagonist group" | CB1 receptor antagonist 0.6 mg/kg | 0.5% methylcellulose/ 0.2% polysorbate |
| 4 | CB1 receptor | sibutramine 3 mg/kg |

-continued

| GROUP | First administration | Second administration |
|---|---|---|
| "combination group" | | antagonist 0.6 mg/kg |

The food consumption of each animal is measured every day. The results are expressed as mean amount of food consumed during the 5 days of treatment. The results obtained are given in the table below.

| Treatment | Food consumption during the 5 days of treatment (g) |
|---|---|
| Vehicles | 25.52 ± 0.30 |
| sibutramine 3 mg/kg | 24.60 ± 0.32* |
| CB1 receptor antagonist 0.6 mg/kg | 24.00 ± 0.24** |
| sibutramine (3 mg/kg) + CB1 receptor antagonist (0.6 mg/kg) | 22.76 ± 0.02*** |

*$p < 0.05$
**$p < 0.01$
***$p < 0.0001$

The results show that, in the animals receiving the sibutramine and CB1 receptor antagonist combination, the reduction in food consumption is much greater has that of the animals treated either with sibutramine alone or with the CB1 receptor antagonist alone.

The compounds of the combination can be employed orally, parenterally, transdermally or rectally, either simultaneously or separately or spread out over time.

The present invention also relates to the pharmaceutical compositions comprising the combination of sibutramine, its hydrate or one of its pharmaceutically acceptable salts and of a CB1 receptor antagonist in the pure state or with one or more compatible and pharmacologically acceptable diluents and/or adjuvants and/or optionally in combination with another pharmaceutically compatible and physiologically active product for a use which is either simultaneous or separate or spread out over time.

Use may be made, as solid compositions for oral administration, of tablets, pills, powders (hard gelatin capsules, cachets) or granules. In these compositions, the active principles are mixed with one or more inert diluents, such as starch, cellulose, sucrose, lactose or silica, under an argon stream. These compositions can also comprise substances other than the diluents, for example one or more lubricants such as magnesium stearate or talc, a colorant, a coating (dragées) or a glaze.

Use may be made, as liquid compositions for oral administration, of pharmaceutically acceptable solutions, suspensions, emulsions, syrups and elixirs comprising inert diluents, such as water, ethanol, glycerol, vegetable oils or liquid paraffin. These compositions can comprise substances other than the diluents, for example wetting, sweetening, thickening, flavouring or stabilizing products.

The sterile compositions for parenteral administration can preferably be solutions in aqueous or nonaqueous form, suspensions or emulsions. Use may be made, as solvent or vehicle, of water, propylene glycol, a polyethylene glycol, vegetable oils, in particular olive oil, injectable organic esters, for example ethyl oleate, or other suitable organic solvents. These compositions can also comprise adjuvants, in particular wetting, isotonizing, emulsifying, dispersing and stabilizing agents. Sterilization can be carried out in several ways, for example by aseptic filtration, by incorporating sterilizing agents in the composition, by irradiation or by heating. They can also be prepared in the form of sterile solid compositions which can be dissolved at the time of use in sterile water or any other injectable sterile medium.

The compositions for rectal administration are suppositories or rectal capsules which comprise, in addition to the active product, excipients such as cocoa butter, semisynthetic glycerides or polyethylene glycols.

The pharmaceutical compositions generally comprise 0.5 to 10 mg of sibutramine and 0.1 to 200 mg of the CB1 receptor antagonist.

The present invention also relates to the method for the treatment of obesity which consists in administering, to the patient, a combination according to the invention either simultaneously or separately or spread out over time.

The doses depend on the desired effect, on the duration of treatment and on the administration route used; they are generally from 1 to 15 mg of sibutramine per day by the oral route for an adult and from 0.10 to 500 mg of the CB1 receptor antagonist per day by the oral route for an adult.

Generally, the doctor will determine the appropriate dosage according to the age, weight and any other factor specific to the subject to be treated.

What is claimed is:

1. A combination of a CB1 receptor antagonist and sibutramine, its hydrate or one of its pharmaceutically acceptable salts, wherein the CB1 receptor antagonist is: 1-[bis(4-chlorophenyl)methyl]-3-[(3,5-difluorophenyl)(methylsulfonyl)methylene]azetidine, or a pharmaceutically acceptable salt thereof.

2. The combination according to claim 1, wherein the components of the combination are administered simultaneously, separately or spread out over time.

3. The combination according to claim 1, wherein each component of the combination is administered in a single dose or in multiple doses.

4. A composition comprising a CB1 receptor antagonist and sibutramine, its hydrate or one of its pharmaceutically acceptable salts, wherein the CB1 receptor antagonist is: 1-[bis(4-chlorophenyl)methyl]-3-[(3,5-difluorophenyl)(methylsulfonyl)methylene]azetidine, or a pharmaceutically acceptable salt thereof and at least one compatible and pharmacologically acceptable diluent or adjuvant.

5. The composition according to claim 4, comprising 0.5 to 10 mg of sibutramine and 0.1 to 200 mg of the CB1 receptor antagonist.

6. The composition according to claim 4, further in combination with a pharmaceutically compatible and physiologically active product.

7. A process for treating obesity in a mammal, comprising administering to the mammal in need thereof an effective amount of at least one CB1 receptor antagonist and sibutramine, its hydrate or one of its pharmaceutically acceptable salts, wherein the CB1 receptor antagonist is: 1-[bis(4-chlorophenyl)methyl]-3-[(3,5-difluorophenyl)(methylsulfonyl)methylene]azetidine, or a pharmaceutically acceptable salt thereof.

8. The process for treating obesity in a mammal according to claim 7, wherein sibutramine is administered at a con centration ranging from 0.5 to 10 mg and the CB1 receptor antagonist is administered at a concentration ranging from 0.1 to 200 mg.

9. The process for treating obesity in a mammal according to claim 7, wherein the CB1 receptor antagonist and sibutramine are administered simultaneously, separately or spread out over time.

10. The process for treating obesity in a mammal according to claim 7, wherein the CB1 receptor antagonist is administered in a single dose or in multiple doses.

11. The process for treating obesity in a mammal according to claim 7, wherein sibutramine is administered in a single dose or in multiple doses.

* * * * *